United States Patent [19]
Basangy

[11] Patent Number: 5,331,739
[45] Date of Patent: Jul. 26, 1994

[54] DISPOSABLE NAIL CUTTING NIPPERS

[76] Inventor: Lea Basangy, 28 Paerdegat 7th St., Brooklyn, N.Y. 11236

[21] Appl. No.: 854,855

[22] Filed: Mar. 20, 1992

[51] Int. Cl.$^5$ .................... A45D 29/02; B26B 17/00
[52] U.S. Cl. .......................................... 30/28; 30/331; 30/338
[58] Field of Search ............... 30/28, 29, 330, 331, 30/334, 337, 338, 261, 262, 260, 162; 132/73, 75.4, 75.5; 254/28

[56] References Cited

U.S. PATENT DOCUMENTS

| | | | |
|---|---|---|---|
| 768,083 | 8/1904 | Sickles | 30/29 |
| 806,037 | 11/1905 | Wilcox | 30/28 |
| 1,580,109 | 4/1926 | Ballou | 30/29 |
| 1,721,415 | 7/1929 | Schnefel | 30/28 |
| 2,028,558 | 1/1936 | Nietzel et al. | 30/28 |
| 3,764,108 | 10/1973 | Dahlin | 254/28 |
| 3,974,999 | 8/1976 | Bertolet | 254/28 |
| 4,034,473 | 7/1977 | May | 30/181 |
| 4,715,121 | 12/1987 | Sugiyama et al. | 30/162 |
| 4,819,673 | 4/1989 | McMullen, Jr. | 30/28 |
| 5,065,516 | 11/1991 | Dulebohn | 30/260 |

FOREIGN PATENT DOCUMENTS 375296  3/1964  Switzerland ............... 30/175

*Primary Examiner*—Douglas D. Watts
*Assistant Examiner*—Hwei-Siu Payer
*Attorney, Agent, or Firm*—Philip Furgang

[57] ABSTRACT

Disposable nail cutting nippers including a body member having a one piece construction to provide first and second gripping portions pivoted about a front hinge portion to be adjacent to each other, and a removable cutting member having cutting blades disposed at the front end portions of the gripping portions. A spring hinge is disposed between the rear end portions of the gripping portions to tension the gripping portions into an open position so that the cutting blades are spaced apart, the gripping portions being squeezed together against the tension of the spring hinge to place the cutting blades in a closed cutting position. Ridges are provided transversely around a periphery of matching central portions of the gripping portions to facilitate the gripping of the body member. A slot is provided in the front hinge portion to removably receive the cutting member therein. The spring hinge includes a tab member having a centrally located, transverse bend therein. In a modified form, the gripping portions are only connected together by the rear spring hinge, where the first gripping portion is U-shaped to provide an open space therein to receive the second gripping portion when the gripping portions are pivoted together about the rear spring hinge, and the front end portions of the gripping portions are each provided with a slot to removably receive the cutting blades. Preferably, the body member is fabricated from a plastic material, and the cutting blades are fabricated from a metal material.

15 Claims, 2 Drawing Sheets

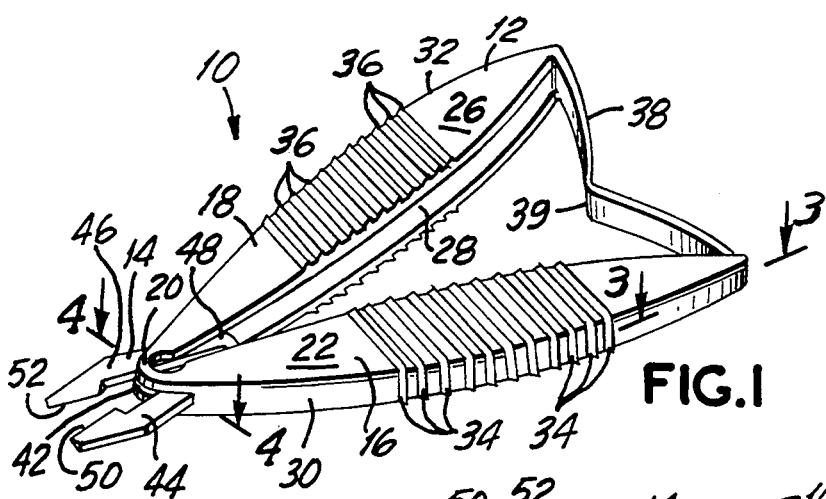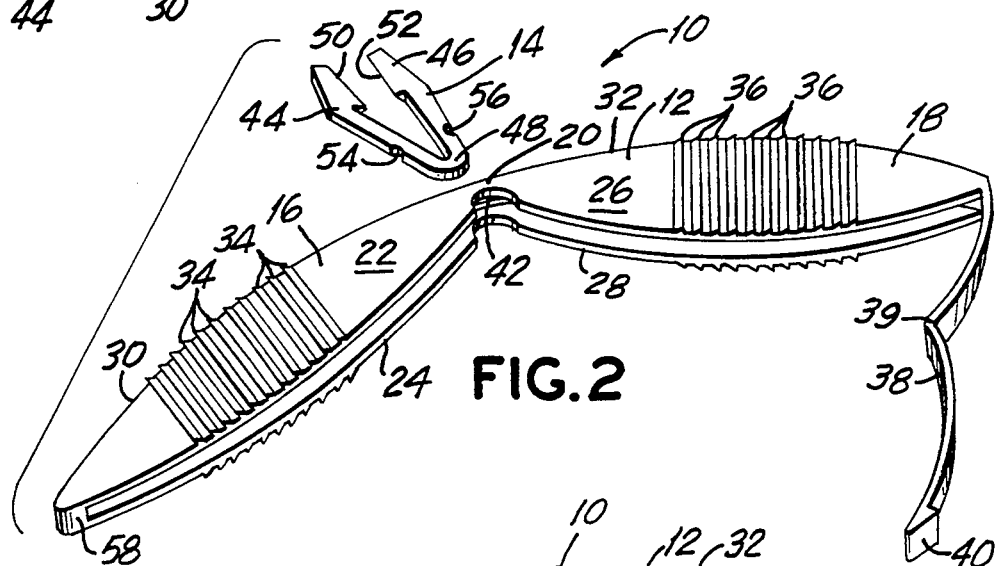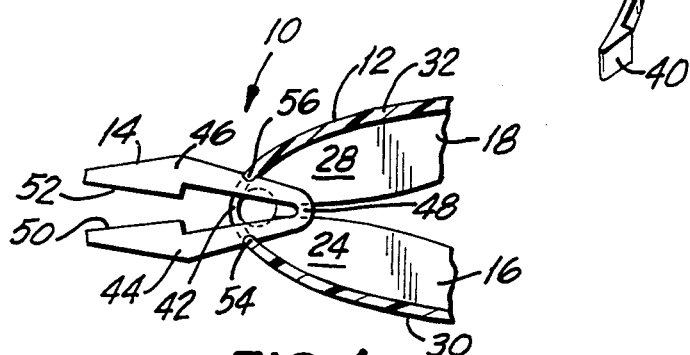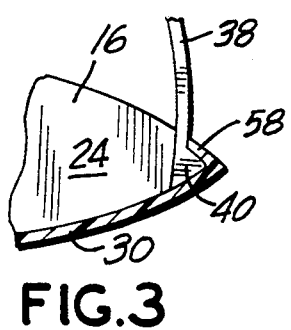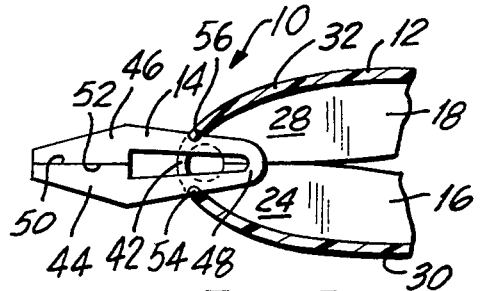

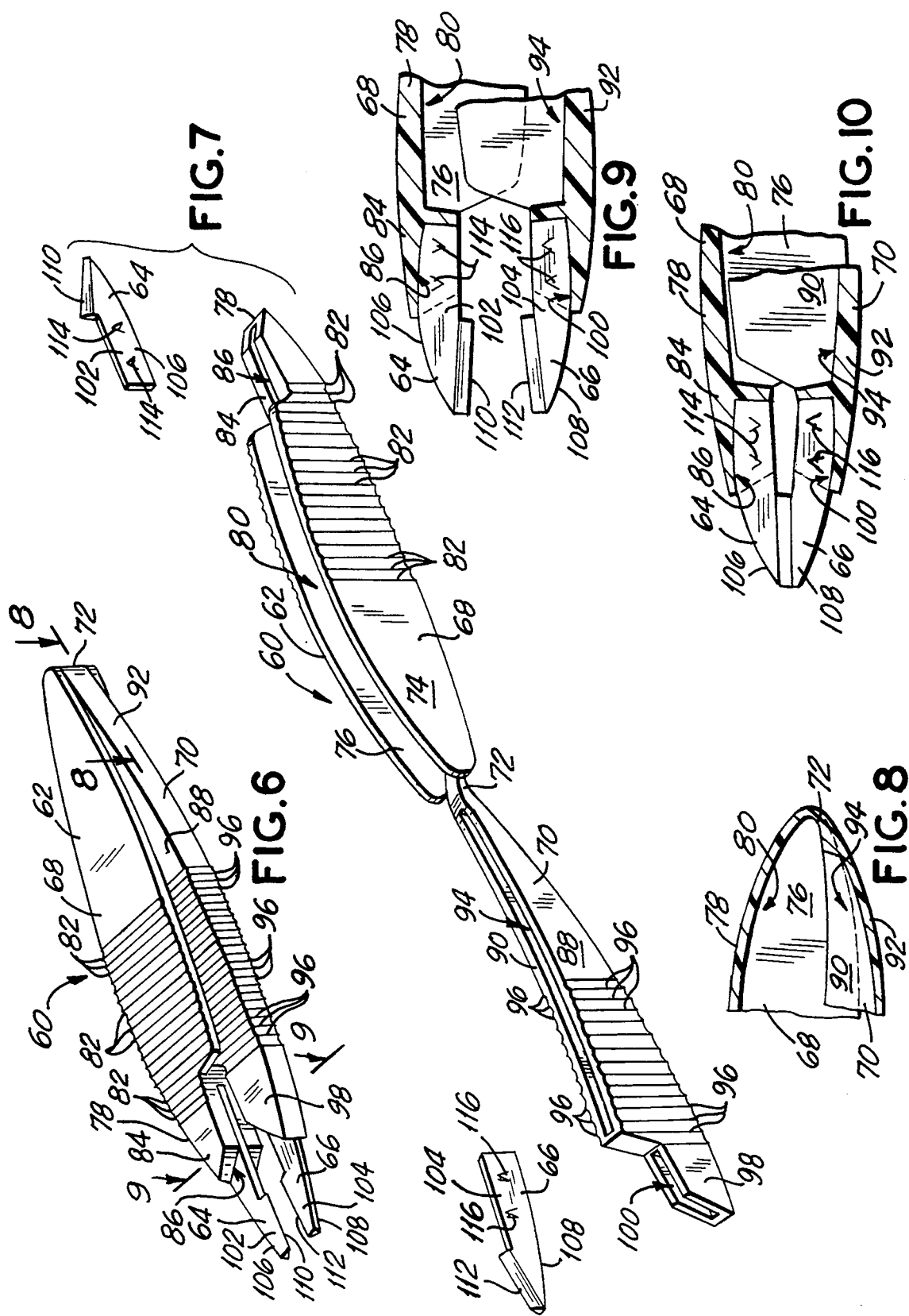

DISPOSABLE NAIL CUTTING NIPPERS

BACKGROUND OF THE INVENTION

The invention relates to nail cutting nippers or clippers, and more particularly, to nail cutting nippers or clippers which are disposable, and which have cutting members which can be removed and disposed of, thus permitting the body member thereof to be used several times before disposal thereof.

Nail cutting nippers or clippers are well known in the art, where most of the prior art devices are fabricated from a metal material and therefore are not of the disposable type, though some do have removable cutting blades. Due to the current fear of contracting AIDS, people are very cautious when it comes to utensils which possibly may come in contact with another person's blood, such being the case when cutting a person's finger nails. Therefore, for the person's safety, it would be recommended that the nail cutting nippers or clippers be disposed of after each time it is used on a particular person, where it would even be helpful if only the cutting blades themselves were disposed of after use on the particular person.

Thus, there is a need for disposable nail cutting nippers which can be used for cutting or trimming a person's nails or cuticles, so that the entire nippers or at least the cutting blades of the nippers can be thrown away after cutting a person's nails or cuticles. Accordingly, if any blood is drawn by the cutting blades, these cutting blades when disposed of cannot contaiminate the next person having their nails and cuticles trimmed or cut.

Most of the prior art devices are in the form of scissors or pliers, where the handles thereof pivot around a pin which connects the handles together. U.S. Pat. No. 770,032, No. 806,037 and No. 1,976,067 disclose nail clippers or cutters in the form of a pair of pliers which are activated by pressing the ends of the handles together, each having removable cutting blades disposed at the opposite ends of the handles, the handles being fabricated from a metal material.

U.S. Pat. No. 4,819,673 discloses a nail clipper having a one piece U-shaped configuration fabricated from a plastic material with removable cutting blades disposed on one side thereof which are connected to a front side edge of each handle, which is activated by squeezing the rear free ends of the handles together, the bight portion at the front end thereof providing a spring hinge at the front end. The nail clipper device of the latter patent contains a safety feature which prevents the user from being cut while clipping his nails, so that there does not appear to be any intention therein to dispose of the nail clipper or the cutting blades thereof after using same on a particular person to avoid being contaminated with AIDS.

SUMMARY OF THE INVENTION

It is accordingly an object of the present invention to provide nail cutting nippers, which avoid the problems of the prior art devices.

Another object of the present invention is to provide nail cutting nippers of the disposable type, which can be thrown away after cutting each person's nails or cuticles.

A further object of the present invention is to provide nail cutting nippers having removable cutting blades, which can be thrown away after cutting each person's nails or cuticles, where new cutting blades can easily be replaced in the nippers.

Yet another object of the present invention is to provide nail cutting nippers, which are inexpensive to manufacture, have few parts, and can be readily assembled.

Still another object of the present invention is to provide nail cutting nippers including a body member having a one piece plastic construction, which include gripping portions which can be squeezed together to force the cutting blades into a closed cutting position.

Another object of the present invention is to provide nail cutting nippers, as described above, which include a spring hinge as part of the body member to tension the gripping portions into the open position with the cutting blades spaced apart.

Yet a still further object of the present invention is to provide nail cutting nippers, as described above, wherein the spring hinge is provided between the rear ends of the gripping portions, and the cutting blades are provided at the front ends of the gripping portions.

Another object of the present invention is to provide nail cutting nippers, as described above, wherein the gripping portions are U-shaped to reduce the cost thereof.

Another object of the present invention is to provide nail cutting nippers, as described above, where transversely extending ridges are provided around the periphery of matching central portions of the gripping portions to facilitate the gripping of the body member.

Briefly, in accordance with the present invention, there is provided disposable nail cutting nippers including a body member having a one piece construction to provide first and second gripping portions pivoted about a front hinge portion to be adjacent to each other, and removable cutting means disposed at the front end portions of the gripping portions. Spring hinge means are disposed between the rear end portions of the gripping portions to tension the gripping portions into an open position so that the cutting means are spaced apart, the gripping portions being squeezed together against the tension of the spring hinge means to place the cutting means in a closed cutting position. Ridge means are provided transversely around a periphery of matching central portions of the gripping portions to facilitate the gripping of the body member. A slot is provided in the front hinge portion to removably receive the cutting means therein. The spring hinge means includes a tab member having a centrally located, transverse bend therein to provide a spring hinge.

In a modified form, the gripping portions are only connected together by the rear spring hinge means, where the first gripping portion is U-shaped to provide an open space therein to receive the second gripping portion when the gripping portions are pivoted together about the rear spring hinge means, and the front end portions of the gripping portions are each provided with a slot to removably receive the cutting means.

Preferably, the body member is fabricated from a plastic material, and the cutting means are fabricated from a metal material.

BRIEF DESCRIPTION OF THE DRAWINGS

With the above and additional objects and advantages in view, as will hereinafter appear, this invention comprises the devices, combinations and arrangements of the parts hereinafter described by way of example and illustrated in the accompanying drawings of preferred embodiments in which:

FIG. 1 is a perspective view of disposable nail cutting nippers in accordance with the present invention;

FIG. 2 is an exploded perspective view showing the parts of the nail cutting nippers of FIG. 1;

FIG. 3 is a cross sectional view taken along line 3—3 of FIG. 1;

FIG. 4 is a cross sectional view taken along line 4—4 of FIG. 1;

FIG. 5 is a cross sectional view similar to the cross sectional view of FIG. 4, showing the cutting blades in the closed cutting position;

FIG. 6 is a perspective view of modified disposable nail cutting nippers in accordance with the present invention;

FIG. 7 is an exploded perspective view showing the parts of the modified disposable nail cutting nippers of FIG. 6;

FIG. 8 is a cross sectional view taken along line 8—8 of FIG. 6;

FIG. 9 is a cross sectional view taken along line 9—9 of FIG. 6; and

FIG. 10 is a cross sectional view similar to the cross sectional view of FIG. 9, showing the cutting blades in a closed cutting position.

In the various figures of the drawings, like reference characters designate like parts.

DESCRIPTION OF THE PREFERRED EMBODIMENTS

Referring now to the drawings, FIG. 1 shows disposable nail cutting nippers 10 according to the present invention. The nippers 10 include a body member 12 and a cutting member 14 which is removably secured to the body member 12, as will be explained below.

As shown in FIG. 2, the body member 12 has a one piece construction, which is preferably molded from a suitable plastic material. The body member 12 includes two substantially similar gripping portion 16, 18 which are integrally joined together by a reduced front hinge portion 20. Each of the gripping portions 16, 18 includes opposing sides 22, 24 and 26, 28, respectively, which are connected by a longitudinally extending edge 30 and 32, respectively, to form a U-shaped construction. Preferably, transversely extending ridges 34 and 36 are provided around the periphery of central mating portions of the gripping portions 16, 18, respectively, to facilitate the gripping of the body member 12.

An elongated tab member 38 extends from the edge portion 32 at the rear end of the gripping portion 18, where preferably the tab member 38 has the same width as the edge portion. The tab member 38 has a centrally located, transverse bend therein to provide a spring hinge 39, as described below. A hook portion 40 is provided at the free end of the tab member 38, as will be explained below. A slot 42 is provided in the edge portion of the hinge portion 20, which also will be explained below. Preferably, the opposing side edges of each of the sides 22, 24 of the gripping portion 16, and of each of the sides 26, 28 of the gripping portion 18, and therefore the edges 30, 32, are bow shaped to facilitate the handling of the nippers 10.

As best shown in FIG. 2, the cutting member 14 has a V-shaped configuration preferably being formed from a flat metal material, such as stainless steel, which is bent into the V-shaped configuration to provide a spring tension between the two leg portions 44, 46 which are connected together by a bight portion 48. Alternately, the cutting member 14 could be a stamped metal part, or could be formed by any other suitable well known method.

Each of the leg portions 44, 46 of the cutting member 14 has a tapered outer edge on the free end portion thereof and a cutting blade 50, 52, respectively, on the inner edge of the free end portion, where the cutting blades 50, 52 project inwardly towards each other. Additionally, a notch 54, 56 is provided in the outer edge of each of the leg portions 44, 46, respectively, the notches 54, 56 being disposed between the cutting blades 50, 52, respectively, and the bight portion 48, the function of which is described below.

As shown best in FIG. 3, the free rear end portion of the gripping portion 16 of the body member 12 has a lip portion 58 extending across the open edge of the gripping portion 16, the lip portion 58 being secured to the sides 22, 24, as shown in FIG. 2. In the assembly of the body member 12, the hook portion 40 of the tab member 38 is inserted into the opened edge of the gripping portion 16 and is hooked behind the lip portion 58 for securement therewith so that the body member 12 is assembled as shown in FIG. 1.

The cutting member 14 is now inserted, the bight portion 48 first, into the slot 42 of the hinge portion 20 from the outside thereof, by squeezing the leg portions 44, 46 of the cutting member 14 together until the end walls of the slot 42 snap into notches 54, 56 of the cutting member 14, as best shown in FIG. 4. It is noted, that when the cutting blades 50, 52 of the cutting member 14 are in the open position, as shown in FIGS. 1 and 4, the distance between the end walls of the slot 42 is approximately equal to the distance between the base walls of the notches 54, 56 of the cutting member 14 so that the cutting member 14 is securely attached to the body member 12, where the leg portions 44, 46 of the cutting member 14 are in a non-tensioned position.

In use, the user grips the body member 12, preferably at the ridges 34, 36, and squeezes the gripping portions 16, 18 together, thereby applying a force on the spring hinge 39 of the tab member 38. During this squeezing action, the end walls of the slot 42 of the hinge portion 20 of the body member 12 are pivoted closer together while seated in their associated notches 54, 56 of the cutting member 14, so that in turn, the leg portions 44, 46 are also squeezed together until the cutting blades 50, 52 are brought together, as shown in FIG. 5. Thus, anything disposed between the cutting blades 50, 52, such as a person's finger nail, will be cut by the cutting blades 50, 52. When the user releases the tension on the gripping portions 16, 18 of the body member 12, both the spring tension in the cutting member 14 and in the spring hinge 39 of the tab member 38 force the cutting blades 50, 52 and the gripping portions 16, 18 to their open non-tensioned positions shown in FIG. 1. The nippers 10 are now ready to be used again to further cut the person's finger nails, where this procedure is repeated until all the finger nails are cut.

After a person's finger nails are cut, the user can either dispose of the entire nippers 10, and use a new nippers 10 for the next person, or the user can merely remove the cutting member 14 from the body member 12 by squeezing the leg portions 44, 46 of the cutting member 14 together until the notches 54, 56 are released, and replace same with a new cutting member 14, as desired, where the body member 12 of the nippers 10 can be used many times before the disposal thereof in that, because of the construction thereof, the body member 12 does not come in contact with any of the persons having their nails cut. Thus, according to the user's discretion, the body member 12 itself can be used as many times as desired, but the cutting member 14 is always replaced for use on each new person.

FIG. 6 shows modified disposable nail cutting nippers 60 according to the present invention. The nippers 60 include a body member 62 and cutting members 64, 66 which are removably secured to the body member 62, as will be explained below.

As shown in FIG. 7, the body member 62 has a one piece construction, which is preferably molded from a suitable plastic material. The body member 62 includes two gripping portions 68, 70 which are integrally joined together by a reduced rear spring hinge portion 72, as will be explained below.

The gripping portion 68 includes opposing sides 74, 76 which are connected by a longitudinally extending edge 78 to form a U-shaped construction to provide an open space 80 therein.

Preferably, transversely extending ridges 82 are provided around the periphery of an intermediate portion of the gripping portion 68 to facilitate the gripping thereof. Preferably, the opposing side edges of each of the sides 74, 76, and therefore the edge 78, are bow shaped to facilitate the handling of the nippers 60. The front end portion of the gripping portion 68 is notch shaped to provide a reduced, projecting front end portion 84. The free end of the front end portion 84 is tapered, and a longitudinally extending slot 86 is provided in the front end portion 84, the function of which will be explained below.

The gripping portion 70 includes opposing sides 88, 90 which are connected by a longitudinally extending edge 92 to form a U-shaped construction having an open slot 94 therein. Preferably, transversely extending ridges 96 are provided around the periphery of an intermediate portion of the gripping portion 70 to facilitate the gripping thereof. As shown in FIG. 6, the ridges 82 of the gripping portion 68 are substantially in alignment to mate with the ridges 96 of the gripping portion 70. It is also preferable that the outer edge 92 is bow shaped to facilitate the handling tof the nippers 60, where the inner side edges of the sides 88, 90 adjacent to the open slot 94 are concave shaped.

The front end portion of the gripping portion 70 is also notch shaped to provide a reduced, projecting front end portion 98. The free end of the front end portion 98 is tapered, and a longitudinally extending slot 100 is provided in the front end portion 98, the function of which will be explained below.

It is noted, that the spring hinge portion 72, as best shown in FIG. 8, is integrally connected to the edge 78 of the gripping portion 68 and the edge 92 of the gripping portion 70 so that the spring tension in the hinge portion 72 maintains the nippers 60 in the open position as shown in FIG. 6, as will further be explained below.

As best shown in FIG. 7, the cutting members 64, 66 are identical, being formed from a flat metal material, where the cutting member 64 has been turned 180° relative to the cutting member 66 shown in this figure. Each cutting member 64, 66 includes a body member 102, 104 having a curved outer edge 106, 108, respectively. A cutting blade 110, 112 is provided on the innter edge of the front end portion of each body member 102, 104, respectively, so that the cutting blades 110, 112 project outwardly therefrom. Additionally, prongs 114, 116-are stamped into the body members 102, 104, respectively, so that the prongs 114, 116 project outwardly from the body members 102, 104, the function of which will be explained below.

The cutting members 64, 66 are inserted into their respective slots 86, 100 of the gripping portions 68, 70, where the curved portions 106, 108 thereof are inserted first. It is noted, that the slots 86, 100 has a width which is preferably slightly less than the thickness of the cutting members 64, 66 so that the cutting members 64, 66 are secured in the slots 86, 100 by a force fit engagement. Additionally, the prongs 114, 116 are pivoted into their respective body members 106, 108 when the cutting members 64, 66 are inserted into the slots 86, 100 so that the inherent spring force of the prongs 114, 116 also acts to secure the cutting members 64, 66 in the slots 86, 100.

After insertion of the cutting members 64, 66, the gripping portions 68, 70 are pivoted about the hinge portion 72 to the open position shown in FIG. 6, where the upper portions of the sides 88, 90 of the gripping portion 70 are received in the open space 80 between the sides 74, 76 of the gripping portion 68. In this open position, the cutting blades 110, 112 are spaced apart as best shown in FIG. 9.

In use, the user grips the body member 62 preferably at the ridges 82, 96, and squeezes the gripping portions 68, 70 together, so that the cutting blades 110, 112 are brought together into a closed cutting position, as shown in FIG. 10. Thus, anything disposed between the cutting blades 110, 112, such as a person's finger nail, will be cut by the cutting blades 110, 112.

When the user squeezes the gripping portions 68, 70 together, the gripping portion 70 moves further into the opening 80 of the gripping portion 68, as indicated in FIG. 10, which thereby applies a tension on the spring hinge portion 72. Thus, when the user releases the tension on the gripping portions 68, 70, the spring hinge portion 72 forces the gripping portions 68, 70 apart to the open non-tensioned position shown in FIG. 6, in which the cutting members 64, 66 are again spaced apart, as best shown in FIG. 9. The nippers 60 are now ready to be used again to further cut the person's finger nails, where this procedure is repeated until all the finger nails are cut.

Here again, after a person's finger nails are cut, the user can either dispose of the entire nippers 60, and use a new nippers 60 for the next person, or the user can merely remove the cutting members 64, 66 from the gripping portions 68, 70 and replace same with new cutting members 64, 66, as desired, where the body member of the nippers 60 can be used many times before the disposal thereof in that, because of the construction thereof, the body member 62 does not come in contact with any of the persons having their nails cut. Thus, according to the user's discretion, the body member 62 itself can be used as many times as desired, but the cutting blades 64, 66 are always replaced for use on each new person.

Numerous alterations of the structures herein disclosed will suggest themselves to those skilled in the art, however, it is understood that the present disclosure relates to preferred embodiments of the invention which are for the purpose of illustration only, and are not to be construed as a limitation of the invention.

What is claimed is:

1. Nail cutting nippers comprising:
   a body member having a one piece construction;

said body member including first and second gripping portions pivoted adjacent to each other;

removable cutting means disposed at front end portions of said first and second gripping portions;

a reduced hinge portion integrally joining said front end portions of said first and second gripping portions together; and spring means disposed between said first and second gripping portions to tension said first and second gripping portions into an open position so that said cutting means are spaced apart;

whereby said first and second gripping portions are squeezed together against the tension of said spring means to place said cutting means in a closed cutting position.

2. Nail cutting nippers according to claim 1, wherein ridge means are provided transversely around a periphery of matching central portions of said gripping portions to facilitate gripping of said body member.

3. Nail cutting nippers according to claim 1, wherein each of said gripping portions is U-shaped to provide opposing sides connected together by a longitudinally extending outer edge.

4. Nail cutting nippers according to claim 1, wherein a slot is provided in said hinge portion to removably receive said cutting means therein.

5. Nail cutting nippers according to claim 4, wherein said cutting means is a V-shaped cutting member having two legs connected together by a bight portion to provide a spring tension between said two legs.

6. Nail cutting nippers according to claim 5, wherein notch means are provided in said two legs of said cutting member to removably receive end walls of said hinge portion slot therein to secure said cutting member of said body member.

7. Nail cutting nippers according to claim 5, wherein a cutting blade is provided on an inner edge of a free end portion of each leg of said cutting member so that the cutting blades project towards each other.

8. Nail cutting nippers according to claim 1, wherein said spring means includes a tab member integrally joined to a rear end portion of said first gripping portion, said tab member having a centrally located, transverse bend therein to provide a spring hinge.

9. Nail cutting nippers according to claim 8, wherein a hook portion is provided on a free end of said tab member, and a lip portion is provided on a rear end portion of said second gripping portion to secure said hook portion to said second gripping portion in a hooked arrangement.

10. Nail cutting nippers comprising:
a body member;
said body member including first and second gripping portions;

pivot means pivotaly securing rear end portions of said first and second gripping portions together;

removable cutting means disposed at front end portions of said first and second gripping portions;

said front end portions of said first and second gripping portions being each provided with a slot to removably receive said cutting means;

said cutting means including a cutting member for each of said first and second gripping portions, the cutting members being fabricated from a flat metal material;

each of said cutting members being provided with prong means to removably maintain said cutting members in associated ones of the slots in said front end portions of said first and second gripping portions; and spring means disposed between and first and second gripping portions to tension said first and second gripping portions into an open position so that said cutting means are spaced apart;

whereby said first and second gripping portions are squeezed together against the tension of said spring means to place said cutting means in a closed cutting position.

11. Nail cutting nippers according to claim 10, wherein ridge means are provided transversely around a periphery of matching central portions of said gripping portions to facilitate gripping of said body member.

12. Nail cutting nippers according to claim 10, wherein each of said gripping portions is U-shaped to provide opposing sides connected together by a longitudinally extending outer edge.

13. Nail cutting nippers according to claim 10, wherein said spring means is a reduced spring hinge portion integrally joining said rear end portions of said gripping portions together, said spring hinge portion providing said pivot means.

14. Nail cutting nippers according to claim 10, wherein each of said cutting members includes a cutting blade so that the cutting blades project towards each other when said cutting members are positioned in associated ones of the slots in said front end portions of said gripping portions.

15. Nail cutting nippers according to claim 10, wherein at least said first gripping portion is U-shaped to provide an open space therein to receive said second gripping portion when said first and second gripping portions are squeezed together.

* * * * *